United States Patent [19]

Cardarelli

[11] 4,228,614
[45] Oct. 21, 1980

[54] FLOATING PESTICIDE DISPENSER

[75] Inventor: Nathan F. Cardarelli, Barberton, Ohio

[73] Assignee: Environmental Chemicals, Inc., Wauconda, Ill.

[21] Appl. No.: 14,118

[22] Filed: Feb. 22, 1979

Related U.S. Application Data

[63] Continuation-in-part of Ser. No. 5,174, Jan. 22, 1979, which is a continuation-in-part of Ser. No. 916,570, Jun. 19, 1978, Pat. No. 4,166,111.

[51] Int. Cl.³ .................... A01M 1/20; A01M 25/00; A01N 55/04
[52] U.S. Cl. ........................................ 43/131; 424/78; 424/83; 424/222; 424/224; 424/288; 424/300
[58] Field of Search ................ 424/78, 83; 43/131

[56] References Cited

U.S. PATENT DOCUMENTS

| | | | |
|---|---|---|---|
| 4,010,141 | 3/1977 | Onozuka et al. | 424/288 X |
| 4,012,221 | 3/1977 | Walker et al. | 71/66 |
| 4,012,347 | 3/1977 | Gitlitz et al. | 424/288 X |

*Primary Examiner*—Leonard Schenkman
*Attorney, Agent, or Firm*—Oldham, Oldham, Hudak & Weber Co.

[57] ABSTRACT

A method and composition for dispensing through a slow release floating polymer a pesticide for destroying aqueous pests, especially mosquito larva. The polymer matrix which has a specific gravity of less than 1.0 so that it floats, may be shaped into any geometric design such as a thin strip or tape and is anchored by an attached weight having a specific gravity greater than 1.0. The floating polymer assures slow release of the insecticide in that it is not covered by debris or silt as would occur with a sinking polymer matrix. The floating matrix can be utilized wherever desirable in slow turnover or stagnant waters, such as in lakes, ponds, swamps, storm sewer catch basins and portable water containers such as rain barrels, and the like. The floating member generally can contain any pesticide for the elimination of any specific pests or insects. The polymer of the matrix is a copolymer of ethylene-vinyl acetate and/or an ethylene-propylene copolymer. Moreover, a coleachant or a porosigen may be utilized to assure continued release over a long period of time such as for one to three years.

65 Claims, 2 Drawing Figures

FLOATING PESTICIDE DISPENSER

CROSS-REFERENCE

This application is a continuation-in-part of my copending application entitled "A Method and Composition for the Long Term Controlled Release of a Non-Persistent Organotin Pesticide from an Inert Monolithic Thermoplastic Dispenser" filed on Jan. 22, 1979 as Ser. No. 5,174, which in turn is a continuation-in-part of an application bearing the same title which was filed on June 19, 1978 as Ser. No. 916,570, now U.S. Pat. No. 4,166,111.

BACKGROUND OF THE INVENTION

The invention relates to the dispersement of a pesticide from a floating plastic matrix in a continuous and controlled manner into water infested with various aquatic pest and insect life. For example, mosquito larva develop through several morphogenetic stages in water, emerging in time as adults capable of transmitting dread diseases which include encephalitis, malaria, yellow fever, filiariasis, dengue fever, and the like, as well as creating a nuisance to man and man's domestic cattle by their proclivity towards biting and other annoyances. Similarly, other insecta, such as flies of the Simulium family, spend their larval stages in water, emerging as adults capable of transmitting onchocerciasis, a dreaded parasitic disease manifested as blindness in exposed human populaces. Snail hosts of parasitic trematodes, as well as the trematode larva, likewise, dwell in water and can similarly be controlled using the invention described in this specification.

The incidence of the above-mentioned various dreaded diseases are increasing in incidence throughout the world. Such increase arises from growing resistance to many insecticides, the ban on major inexpensive control agents such as DDT, and the economics of control and eradication. A significant contribution to increased incidence of such diseases is through lack of mosquito control. Mosquito breeding sites are of many kinds, some being easily amenable to treatment with insecticides and others being inherently difficult to treat or very expensive to so treat. In the latter category are storm or catch basins, containers used for portable water supplies, generally stagnant ponds, swamps, and the like. As described in the monumental text by Cardarelli, 1976, and is now well known to the pesticide formulation and used in the art, through the incorporation of select pesticides in select polymeric matrices, it is possible to cause a slow-long duration release of ultra-low concentrations of said pesticides in the pest-infected environment with efficacious benefit and much reduced environmental impact. When target organisms are continuously exposed to very low toxicant concentrations, such concentrations being far too small to materially affect insect control, the gradual accumulation of such agents in the pest body leads to a chronic manifestation of intoxication and eventual mortality.

Slow release toxicant compositions, such as those taught in U.S. Pat. Nos. 3,639,583 and 3,417,181, rely upon release being affected through the now well known and understood diffusion-dissolution mechanism. It is taught in said patents that release is critically dependent upon the binding polymeric matrix being a solute for the organotin classes used. The binder matrix is a vulcanized or a plurality vulcanized elastomer. However, it is well known that generally organotins totally lack solubility in thermoplastic materials and, thus, the diffusion-dissolution process cannot be established.

U.S. Pat. No. 4,012,221 relates to inorganic copper salts capable of releasing copper salts in water with the copper salts being dispersed in a moderate crosslinked elastomer in which the copper salts are insoluble.

In other inventions, it has been taught that the pesticidal agents such as oganophosphorus class insecticides will similarly release from solute matrices, especially from elastomers. U.S. Pat. No. 3,590,119 is an example of this teaching.

Many mosquito larvicides are known and used in both the conventional sense as well as in controlled release methodologies such as microencapsulation. Among others, Boike et al has shown in examining 23 different organotin formulations in solute elastomer formulations, that they are not effective against the mosquito under practical use situations due to the presence of natural organic substances common to water courses. Said organic materials rapidly absorb organotin molecules, essentially removing them from mosquito larva contact.

U.S. Pat. No. 3,705,938 teaches that several organophosphorus-type insect adulticides can be incorporated in a laminated polyvinyl chloride structure, wherein no agent solubility exists, and caused to move continuously through said plastic structure to said plastic surface through a volatility mechanism wherein the medium of release is air. Such constructions require the use of a third phase material such as a plasticizer to effect toxicant movement.

U.S. Pat. No. 4,012,347 relates to the antifouling performance of certain asymmetric triorganotin compounds which are incorporated into a coating composition a film-forming polymer, a rosin, a solvent, as well as a pigment. Although various film-forming polymers are disclosed including elastomers, the use of an ethylene-vinyl acetate copolymer is not taught. Moreover, the invention leaching rate is very dependent upon the ratio of the rosin to the various polymers.

U.S. Pat. No. 3,234,032 also relates to an antifouling marine coating composition wherein various organotin compounds are combined within the film-forming vehicles such as waxes, oils, or a paint having a synthetic polymeric material. Such synthetic materials are the vinyl polymers, the acrylic polymers and the alkyd polymers. Hence, no suggestion of applicant's specific copolymer or coleachant system is taught.

U.S. Pat. No. 3,236,793 relates to a bis(tributyltin)-adipate antifouling composition wherein the tin compound is dispersed in a substantially water-insoluble film-forming vehicle such as spar varnish, vinyl acetate - vinyl chloride copolymer-based paints, and the like. Obviously, this patent is unrelated in that it relates to a completely different type of organotin compound and lacks any suggestion of a coleachant system as well as an ethylene-vinyl acetate copolymer.

Yet another prior art vehicle is that appearing in CHEMICAL ABSTRACTS, 75:97577c (1971) wherein various non-organotin liquid pesticides are dispersed in various film-forming polymers. Once again, this prior art article is readily distinguished from the present invention in that it lacks at least applicant's specific copolymer, organotin compound, as well as the coleachant system.

SUMMARY OF THE INVENTION

Accordingly, it is an object of the present invention to provide a floating dispenser containing a slow release pesticide for destroying pests by incorporating a pesticide into a thermoplastic compound.

It is another object of the present invention to provide a floating pesticide dispenser, as above, wherein said floating pesticide dispenser can be utilized in catch basins, potable water storage barrels or tanks, ponds, lakes, swamps, marshes, culverts, and any other aqueous environment having slow-moving or stagnant water.

It is a further object of the present invention to provide a floating pesticide dispenser, as above, wherein said floating portion is anchored (generally through a weight) to the bottom of the aqueous environment.

It is an additional object of the present invention to provide a floating pesticide dispenser, as above, wherein said floating dispenser can be directly attached to the anchor and be in the form of strands, coils, and the like, or attached to the anchor at a distance as through a connecting member, for example, a line or the like.

It is still another object of the present invention to provide a floating pesticide dispenser, as above, wherein the thermoplastic compound is a copolymer of ethylene-propylene, a copolymer of ethylene-vinyl acetate, or combinations thereof.

It is a still further object of the present invention to provide a floating pesticide dispenser, as above, wherein said thermoplastic compound contains a coleachant or a porosigen which acts as a porosigen, thus slowly creating the need-fed pore structure for toxicant emission.

It is still an additional object of the present invention to provide a floating pesticide dispenser, as above, which generally destroys aquatic pests or aquatic breeding pests.

It is yet an additional object of the present invention to provide a floating pesticide dispenser, as above, which effectively destroys mosquito larva.

It is yet an additional object of the present invention to provide a floating pesticide dispenser, as above, wherein the pesticide is a halogenated trialkyl organotin.

It is yet another object of the present invention to provide a floating pesticide dispenser, as above, in which said pesticide is tetramethyl-O,O-thiodi-p-phenylene phosphorothioate; 2-(1-methylethoxy)phenol methylcarbamate; O,O-diethyl-O-(3,5,6-trichloro-2-pyridyl) phosphorothioate; or O,O-dimethyl phosphorodithioate ester of diethyl mercaptosuccinate.

These and other objects of the invention will become apparent from the specification.

Generally, a floating pesticide dispenser, comprises: a dispenser containing a pesticide, said dispenser having a density of less than 1.0 grams per cc so that it floats; and a weighted anchor connected to said float means, said anchor having a density greater than 1.0 grams per cc.

Additionally, a floating pesticide dispenser, comprises: a dispenser containing pesticide and having a density less than 1.0 grams per cc, said dispenser containing a thermoplastic copolymer, said thermoplastic copolymer selected from the class consisting of a copolymer of ethylene-vinyl acetate, a copolymer of ethylene-propylene, and combinations thereof, said ethylene-vinyl acetate copolymer having from about 60 percent to about 95 percent by weight of ethylene and a weight average molecular weight of from about 40,000 to about 400,000, said ethylene-propylene copolymer having from about 30 percent to about 80 percent by weight of ethylene, and a weight average molecular weight of about 50,000 to about 250,000, said dispenser containing a pesticide for destroying aquatic pests and plants, and a weighted anchor, said weighted anchor connected to said float so that said float is maintained within a confined area and said pesticide is slowly released from said thermoplastic dispenser.

Generally, a process for destroying pests by the gradual and continued release of a pesticide from a floating pesticide dispenser, comprises the steps of: preparing a mixture of the pesticide and a polymer matrix, said dispenser having a density of less than 1.0 grams per cc and containing a thermoplastic copolymer, said themoplastic copolymer selected from the class consisting of a copolymer of ethylene-vinyl acetate, a copolymer of ethylene-propylene, and combinations thereof, said ethylene-vinyl acetate copolymer having from about 60 percent to about 95 percent by weight of ethylene and a weight average molecular weight of from about 40,000 to about 400,000, said ethylene-propylene copolymer having from about 30 percent to about 80 percent by weight of ethylene and a weight average molecular weight of from about 50,000 to about 250,000; connecting a weighted anchor to said float so that said float is maintained within a confined area; and applying said float containing said weighted anchor to an aqueous environment so that said pesticide egresses from said polymer matrix.

DESCRIPTION OF THE PREFERRED EMBODIMENTS

The present invention relates to the sustained release of a pesticide in a floating thermoplastic compound which is very effective against aquatic pests, aquatic plant life, as well as pests which spend a portion of their life in water or upon the surface of water, such as mosquito larva and can also be utilized against molluscan hosts of trematode parasites and the like. The floating pesticide dispensing compound permits a long duration controlled release of the particular pesticide in ultralow concentrations in water that results in the gradual accumulation of said agents within the responsive pest target with resulting chronic intoxication and eventual mortality. A highly preferred pesticide is tetramethyl-O,O'-thiodi-p-phenylene phoephorothioate, commonly referred to as Temephos, which is very effective against mosquito larva. Another preferred pesticide is an organotin which is effective not only against mosquito larva, but various molluscs as well, and has the formula $R_3Sn_nX$, wherein $R_3$ is an alkyl group having from 1 to 8 carbon atoms, desirably from 3 to 6 carbon atoms, with preferably 3 carbon atoms, that is propyl and the isomers thereof being preferred. An alkyl group containing 4 carbon atoms, that is butyl and the various isomers thereof is highly preferred. Additionally, the organo portion R of the tin toxicant may be an aryl group or a substituted aryl group with the substituted portion being an alkyl or an ester group containing from 1 to 6 carbon atoms. Specific examples of such compounds include phenyl, phenyl acetate, phenyl propionate, phenyl isobutyrate, and the like.

The anion or "X" portion of the organotin compound can be a halogen, an oxide, an alkoxy $OR^1$, wherein $R^1$ is an alkyl and contains from 1 to 12 carbon atoms, or an

group where R" is an alkyl having from 1 to 12 carbon atoms such as propionate, butyrate, pentyate, hexylate, and the like with acetate being preferred. Of the various anions, the halogens are preferred with fluorine being highly preferred.

Another effective pesticide is 2-(1-methylethoxy)-phenol methylcarbamate, commonly known as Baygon, manufactured by Mobay Chemical Company of Kansas, Mo., O-O-diethyl-O-(3,5,6-trichloro-2-pyridl)phosphorothioate, commonly known as Dursban; and the O,O-dimethyl phosphorodithioate ester of diethyl mercaptosuccinate, commonly known as Malathion.

Figure 1:
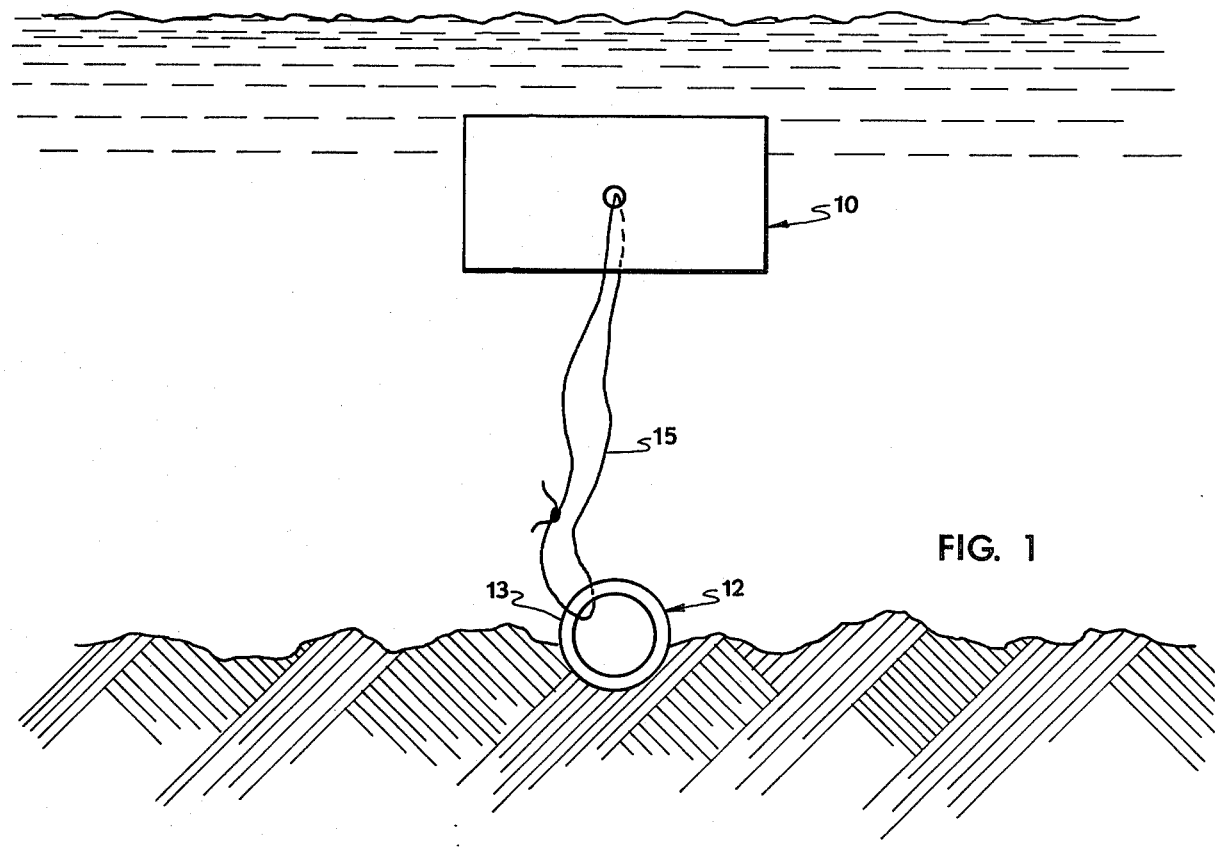
FIG. 1 is a cross-sectional view showing a floating chip attached via a line to a weighted anchor which is resting on the bottom of a body of water.
Figure 2:
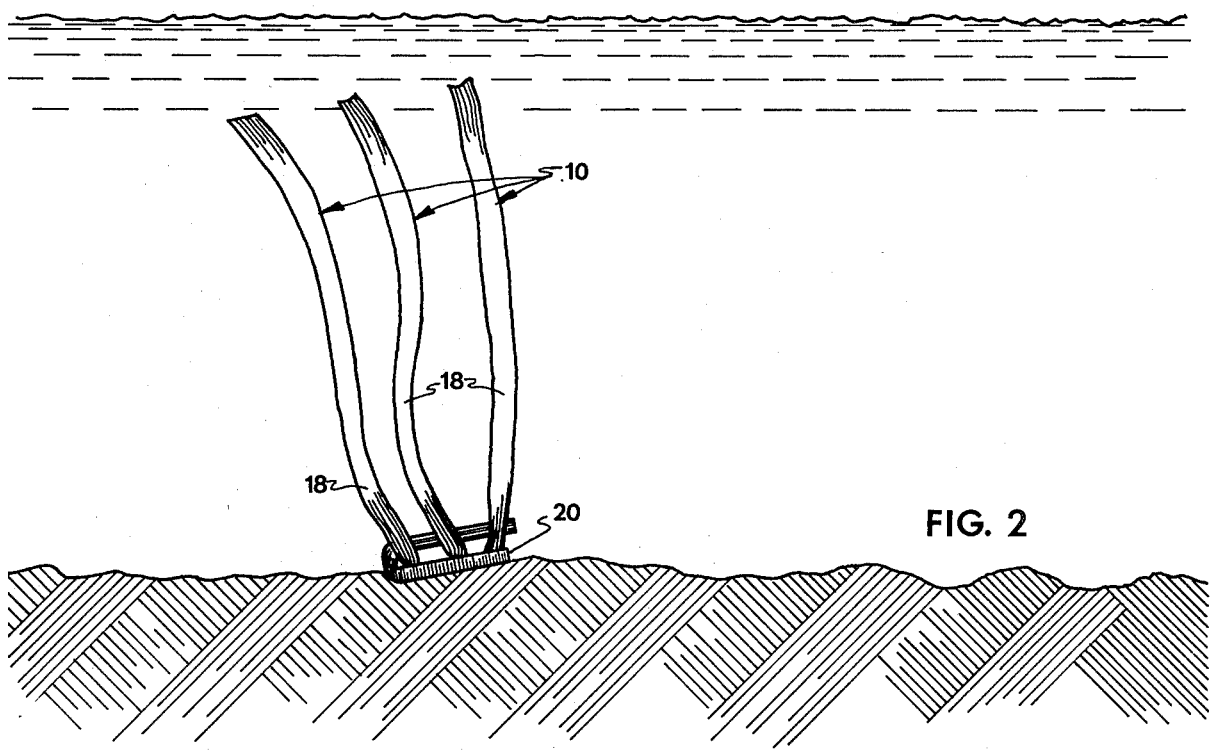
FIG. 2 is a cross-sectional view similar to FIG. 1 wherein the floating pesticide dispenser is in the form of strands which are attached to a weighed anchor as in the form of a metal crimp.

The floating pesticide dispenser of the present invention is generally indicated by the number 10 of FIGS. 1 and 2. The floating dispenser has a density less than 1.0 grams per cc. The density can be controlled through proper selection of components as well as the use of common and conventional blowing agents known to those skilled in the art such as Celogen, which degrade at a temperature at which the floating pesticide dispenser or composition can be extruded without degrading the components thereof. In order to ensure that floating dispenser 10 is not washed or floated away in various aquatic environments, but contained in a confined area, it has an anchor, generally indicated by the numeral 12, as in the form of a weight 13. A string or line 15 extends between the floating dispenser or chip and the weight in any desirable length and connects these two structures. The density of the anchor is generally in excess of 1.5 grams per cc and may be any item such as steel, for example, a washer, or a metal crimp, and generally any metal or other item which serves as a suitable ballast. Desirably, the length of the line is such as to preclude silting over due to the input of various sorts of debris in the particular aqueous environment.

The floating pesticide dispenser, as shown in FIG. 1, thus resides within the aqueous body and can be made to reside within the infraneustral zone where mosquito larva spend most of their time before emergence. Moreover, depending upon the length of connecting line 15, floating pesticide dispenser 10 can be made to always float upon the water surface (not shown) regardless of typical variations in level of the water depth. This factor also affords a visible inspection.

A second structure for suspending a floating controlled release pesticide dispenser is shown in FIG. 2. In this embodiment, floating pesticide dispenser 10, which has a density of less than 1.0 grams per cc, is processed as an extruded strand, rope or the like. One or more strands 18 are clamped together through fastener 20 which may be a metal crimp or generally any compound having a density of 1.5 grams or greater as well as a mass greater than that of a total number of extending strands 18. Naturally, strands 18 have a length conducive to their end use, and sufficient to avoid coverage as by silt or debris. The crimp is of suitable geometry to prevent the strands from washing away as through flooding. Moreover, several strands may be held together as by having an enlarged bottom portion (not shown) so that a mechanical binding occurs at the fastener through which the strands cannot pass. Of course, strands may also be crimped in the center so that one length of strand becomes two strands.

Naturally, the amount of pesticide in the floating chips or strands can be readily calculated to yield a suitable dispersion of the pesticide for a specific volume of water and a specific strand surface area. Obviously, the chip or strands can be of numerous sizes, for example a chip of 2 inches×1 inch×1/16 inch thickness or a strand as from 8 to 24 inches in length by 1/32 to 1/16 inch diameter.

Regardless of specific type, shape, form, etc. of anchor utilized, it generally is from two to ten times the weight of the float. The connecting line moreover can be of any suitable metal such as polyester, nylon, polypropylene, fish line, or other resistant material.

The chips or strands are processed by blending the pesticide with a thermoplastic compound and also preferably with a coleachant. An extruder is very handy for such a blending and processing operation and produces a product which has very desirable and consistent controlled release properties.

As noted, a highly preferred pesticide is tetramethyl-O,O'-thiodi-p-phenylene phosphorothioate, which is commercially available as Temephos as manufactured by the Cyanimid Co. This pesticide is considered as being water insoluble in that its solubility is only about 25 parts per million in water, and yet it is generally effective with regard to controlling mosquito larvacide, when existing in very small amounts such as down to about 0.03 parts per million of water.

Based upon 100 parts of a thermoplastic compound set forth below, the amount of Temephos ranges from about 2 parts to about 80 parts by weight, desirably from about 3 parts to about 50 parts and preferably from about 5 parts to about 20 parts by weight.

The other previously noted pesticides such as Baygon, Dursban and Malathion are commercially available and can be utilized in the same amounts as Temephos. Moreover, any other pesticide known to the art which is effective in water may also be utilized.

The organotin pesticide generally possesses low to very low water solubility and no thermoplastic solubility. In the present invention, the organotin toxicant is generally monolithically dispersed in association with the porosity enhancing coleachant.

The specific organotin compound of the present invention has the formula $R_3Sn_nX$ where R, the organo group, is an alkyl group having from 1 to 8 carbon atoms, desirably from 3 to 6 carbon atoms, with preferably 3 carbon atoms, that is propyl and the isomers thereof being preferred. An alkyl group containing 4 carbon atoms, that is butyl and the various isomers thereof, is highly preferred. Additionally, the organo portion (R) of the tin toxicant may be an aryl group or a substituted aryl group with the substituted portion being an alkyl or an ester group containing from 1 to 6 carbon atoms. Specific examples of such compounds include phenyl, phenyl acetate, phenyl propionate, phenyl isobutyrate, and the like. The anion or "X" portion of the organotin compound may be a halogen, an oxide, an alkoxy OR' wherein R' is an alkyl and contains from 1 to 12 carbon atoms, or an

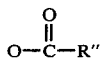

group wherein R" is an alkyl having from 1 to 12 carbon atoms such as propionate, butyrate, pentyate, hexylate, and the like with acetate being preferred. Of the various anions, the halogens are preferred with fluorine being highly preferred. Thus, a highly preferred alkyl compound of the present invention is tributyltin fluoride. Desired aryl compounds are triphenyltin fluoride and triphenyltin acetate.

The solubility of the organotin compounds in a thermoplastic matrix or binder is nil, as noted, and very low in water; that is, approximately 3 parts per million by weight or less. The amount of organotin compound utilized by weight per 100 parts of polymer matrix binding agent ranges from about 25 parts to about 75 parts, with from about 40 parts to 70 parts being preferred. Naturally, smaller or higher amounts may be utilized, but these ranges result in very effective pest-toxicant thermoplastic matrixes.

The termoplastic compound floating pesticide dispenser 10, also known as the polymer matrix or binding agent of the present invention, contains an ethylene-vinyl acetate copolymer. Such a copolymer is readily available in commerce and the amount by weight of the ethylene units, based upon the total weight of the copolymer, ranges from about 60 percent to about 95 percent with a range of from about 80 percent to about 93 percent being preferred. The weight average molecular weight of the copolymer generally ranges from about 40,000 to about 400,000 and preferably from about 75,000 to about 300,000. Desirably, the copolymer has an ASTM Test #D1238 melt flow index of from about 6 to about 12 and preferably from about 7 to about 11 and a Vicat softening point of from about 70° C. to about 95° C. Since, apparently, the ethylene repeating units in the copolymer act as a regulator with regard to pore size, higher amounts of the ethylene constituent will result in slower release times.

Additionally, a polymer matrix or binding agent which can be utilized alone or in combination with said ethylene-vinyl acetate copolymer is an ethylene-propylene copolymer having a weight average molecular weight of from about 50,000 to about 250,000 with a preferred range of from about 100,000 to about 200,000. The percent by weight of the ethylene units can generally vary from about 30 percent to about 80 percent and preferably from about 45 percent to about 75 percent. The melt flow index of the ethylene-propylene copolymer can generally range from about 15 to about 45, and preferably from about 20 to about 32 according to ASTM Test #D1238 at 190°, 21600 gm,gm/10 minutes.

Moreover, in order to promote long release duration, it has been found useful, although not necessary, to blend the ethylene-vinyl acetate copolymer or the ethylene-propylene copolymer, or combinations thereof, with a polyethylene, especially low density polyethylene (that is, a density of from about 0.90 to 0.94 g/cc), having a melt flow index similar to said ethylene-vinyl acetate copolymer, that is from about 5 to about 14 and, preferably, from about 7 to about 11, and a weight average molecular weight of from about 100,000 to about 400,000. Thus, depending upon the rate of release, various amounts of low density polyethylene may be utilized. Generally, to obtain desirable release rates, the amount of homopolyethylene utilized may range from about 30 percent to about 75 percent and, preferably, from about 40 percent to about 60 percent by weight based upon the total weight of the blend of the ethylene-vinyl acetate copolymer, or the ethylene-propylene copolymer, or combinations thereof, and the polyethylene.

A number of moderate or low solubility compounds can be utilized as a coleachant or porosity-inducing agent. By moderate or low solubility, it is meant that the solubility is approximately 0.1 or less and preferably 0.01 grams or less per 100 grams of water. Generally, any compound which is inert with respect to the polymer matrix and the pesticide can be utilized. By inert, it is meant that the coleachant does not chemically react with the polymer matrix or the pesticide. Additionally, the coleachant is also not damaging or harmful to the environment such as the various mercury, cadmium, arsenic compounds, and the like. Thus, the coleachant can be any compound which meets the requirements and is set forth in the Handbook of Chemistry and Physics, 1977-78 Edition, published by the Chemical Rubber Co., which is hereby fully incorporated by reference. A suitable class of an inert coleachant or a porosigen compound includes the inorganic salts or oxides. The cation of such a salt may generally be any of the alkaline metals and preferably any of the alkaline earth metals, Column 1A and 2A, respectively, of the Periodic Table. Additionally, various other metals may be utilized such as iron, nickel, zinc, tin, silver and the like. The anion portion of the salt may generally be any given negative charge entity as the various carbonates, the various nitrates, nitrites, or nitrides, the various sulfates, sulfites, or sulfides, the various phosphates, phosphites, or phosphides, including the ortho, pyro, hypo, variations thereof, and the like. Generally, the sulfates, sulfites and sulfides are preferred as anions, with carbonates being highly preferred. Moreover, as noted above, the anion may be an oxide of the metal. Specific examples of coleachants or a porosigen include magnesium carbonate, magnesium sulfide, magnesium phosphide, magnesium oxide, calcium carbonate, calcium bicarbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, iron carbonate, iron sulfate, iron sulfide, iron sulfite, nickel carbonate, nickel sulfide, zinc carbonate, zinc oxide, zinc sulfide, zinc sulfite, tin sulfide, tin oxide, silver carbonate, silver oxide, silver sulfide, silver sulfite, lithium phosphate, beryllium oxide, strontium carbonate, strontium sulfate, and strontium sulfite. Additionally, silicon dioxide may also be utilized. Magnesium carbonate, strontium carbonate, ammonium carbonate, barium carbonate are preferred, with calcium carbonate and ammonium sulfate being highly preferred. The amount of coleachant or a porosigen generally varies from about 15 parts to about 70 parts by weight based upon 100 parts of said polymer matrix (that is, said copolymer or said blend of said polyethylene and said copolymer), and preferably from about 25 to about 60 parts, when an organotin compound is utilized. When the pesticide is Temephos, Dursban, Malathion, Baygon, and the like, the amount of the coleachant on a porosigen generally varies from about 5 to about 70 parts by weight with from about 15 to about 35 parts being preferred.

It is desirable at times to use a coleachant or a porosigen compound having a solubility greater than 0.1 grams per 100 grams of water whenever utilizing an insecticide which has a very low solubility in water in order to enhance the discharge or leaching rate from the polymer matrix. For example, Temephos has a lower solubility in water than does the organotin compound. Generally, any inert and non-environmental harmful compound can be utilized which has a solubility of from 0.1 to 1 gram as well as from 1.0 to about 100 grams per 100 grams of water. Examples of such high solubility compounds are set forth in the Handbook of Chemistry and Physics, 1977–78 Edition, published by the Chemical Rubber Company which is hereby fully incorporated by reference. Generally, the halogen salts of the above-listed metals are desirable. Additionally, the ammonia salts constitute another class with specific examples being ammonium bromide, ammonium carbonate, ammonium chlorate, ammonium chloride, ammonium fluoride, ammonium sulfate and the like. Of this group, ammonium carbonate is preferred with ammonium sulfate being highly preferred. Although the high solubility coleachant may be utilized by itself as in an amount from 1 to about 60 parts, and preferably from 2 to about 20 parts, it is generally used in association with the low solubility compounds as in an amount from 0.2 to about 25 parts, desirably from 0.5 to about 10 parts, and preferably from about 0.6 to about 4.0 parts.

The composition can contain, in addition to the abovementioned component, various well known and conventional additives to enhance dispersion, add color, aid in processing, or to alter density. For example, zinc stearate may be utilized as a dispersant in suitable amounts as from 0.2 parts to about 10 or 20 parts by weight per 100 parts by weight of polymer. As previously noted, Celogen or any other conventional blowing agent may be utilized to decrease the density of floating dispenser 10. Furthermore, the composition can contain suitable amounts of an attractant-porosigen such as from about 12 to about 25 parts of soy oil or lecithin when not utilized in an aqueous environment. Additionally, carbon black may be utilized as a regulant.

In order to form a suitable thermoplastic dispenser which releases suitable amounts of an organotin pesticide through a coleachant system, it is desirable that the particle sizes of the various components be relatively small. For example, it is desirable that the pesticides such as organotin compounds have a Tyler mesh size of roughly 100 or greater (i.e., a particle size smaller than 100 mesh) and preferably smaller than 200 mesh. Accordingly, a particle size range for the coleachant is generally the same. The particle size of the ethylene-vinyl acetate copolymer, the polyethylene, and the ethylene-vinyl acetate copolymer is roughly about 50 to 200 Tyler mesh. Since the composition is made by heating and melting the polymer, the polymer size is not very important.

The floating chip pesticide is prepared by mixing the pesticide compound with the copolymer matrix and the optional but preferred coleachant in suitable proportions as indicated above in any conventional mixing apparatus along with various additives such as colorants, dispersants, and the like. The mixture is then coalesced by heating at least above the softening point and preferably above the melting point of the copolymer matrix as partitioned for use in any suitable size or shape, for example, chip or ribbon form. Thus, the mixture may be added to a conventional extruder where it is molded at from about 130° C. to about 190° C. in a suitble form such as a ribbon where it may be cut into chips.

The invention will be better understood by reference to the following examples.

EXAMPLES

The formulations listed in Table I were mixed by tumbling or in a high speed blender, added to the hopper of conventional plastic extruder and then extruded as a ribbon of 1 inch width by 0.02 inch thickness. Since the relase rate is proportional to the surface area, the surface to volume ratio is a major determination of lifetime. Consequently, the extruder ribbon is made to predetermine dimensions commensurate with a desired biocidal lifetime.

TABLE I

| INGREDIENT | A | B | C | D | E | F | G | H | I | J |
|---|---|---|---|---|---|---|---|---|---|---|
| Vistalon 702[1] | 34.0 | 36.6 | 37.6 | 36.8 | 75.5 | 44.8 | 42.1 | — | — | 37.5 |
| Microthene 718[2] | 34.0 | 36.6 | 37.6 | 36.8 | — | 44.8 | 42.1 | 76.0 | — | — |
| Zinc Stearate | 0.2 | 1.8 | 1.9 | 1.8 | 1.9 | 2.2 | 2.2 | 1.9 | 1.9 | 1.9 |
| EVA 763[3] | — | — | — | — | — | — | — | — | 75.3 | 37.5 |
| Calcium Carbonate | 16.5 | 15.0 | 17.6 | 17.0 | 18.3 | — | — | 14.5 | 14.4 | 15.6 |
| Ammonium Sulfate | 1.0 | — | — | 2.5 | — | — | 5.2 | — | — | — |
| Silicon Dioxide | 6.1 | — | — | — | — | — | — | — | — | — |
| Celegen | — | 2.0 | — | — | — | — | — | — | — | — |
| Temephos[4] | 8.2 | 8.0 | 5.3 | 5.1 | 4.3 | 8.2 | 8.4 | 7.6 | 8.4 | 7.5 |

[1] An ethylene-propylene copolymer having a melt flow index of 27, manufactured by Exxon Chemical Co., U.S.A.

[2] A low density polyethylene having a density of 0.917 gms/cc and a melt flow index of 8.5, manufactured by U.S.I. Chemicals.

[3] Ethylene-vinyl acetate copolymer having a melt flow index of 90, manufactured by U.S.I. Chemicals.

[4] Used as 90 percent technical trade, tetramethyl-O,O-thiodi-p-phenylene phosphorothioate, manufactured by American Cyanamid Co.

In one test for efficacy, 1 inch × 1.5 inch chips were cut to a small size, weighed and immersed in 1 liter of water for stated periods of time, removed and evaluated against 10 or 15 mosquito larva of first or second instar. Bioassay is performed in replicates. Mortality is observed daily and the lethal time to the 100 percent mortality level is noted below in Table II in order to illustrate the long term continuous release characteristic of one of the formulations.

TABLE II

LONG TERM IMMERSION STUDY OF FORMULATION A

| Pretest Immersion Time | LT$_{100}$ (days) by Active Agent Concentrations (ppm)* | | | | | | | | | | |
| --- | --- | --- | --- | --- | --- | --- | --- | --- | --- | --- | --- |
| | 0.035 | 0.06 | 0.14 | 0.23 | 0.46 | 0.54 | 0.84 | 1.3 | 1.5 | 2.2 | 3.4 |
| LT$_{100}$ (days) | | | | | | | | | | | |
| 30 days | 6 | 5 | 5 | 2 | 2 | 2 | 3 | 2 | 3 | 2 | 2 |
| 70 days | 11 | 9 | 6 | 4 | 4 | 3 | 3 | 3 | 3 | 3 | 2 |
| 110 days | 10 | 13 | 7 | 8 | 8 | 3 | 3 | 5 | 4 | 3 | 2 |
| 160 days | 11 | 9 | 11 | 4 | — | 6 | 6 | 3 | 1 | 2 | 1 |
| 225 days | 14 | 9 | 5 | 4 | 4 | 4 | 5 | 7 | 3 | 2 | 1 |
| 310 days | — | — | — | — | — | — | 5 | 3 | 6 | 3 | 3 |

*Values given are for the total agent content in the test specimen used and not for the amount present at any given time in water.

As readily apparent from Table II, it can be seen that 100 percent mortality was achieved in generally periods of from 1 to about 10 days with some very low concentrations requiring slightly longer periods of time.

The third table compares the several Temephos formulations for efficacy against first and second instar *Culex pipiens quinquefasciatus*.

TABLE III

LARVICIDAL EFFICACY OF SEVERAL CONTROLLED-RELEASE TEMEPHOS FORMULATIONS

| FORMULATION | Conc.¹(ppm) | LT$_{100}$ (No Previous Immersion) | |
| --- | --- | --- | --- |
| | | 1.0 | 0.1 |
| A | | 2 days | 7 days |
| B | | 0.5 days | 1.0 days |
| C | | 3 days | 4 days |
| D | | 1 day | 4 days |
| E | | 1 day | 3 days |
| F | | 2 days | 3 days |
| G | | 1 day | 1 day |
| H | | 1 day | 4 days |
| I | | 1 day | 3 days |
| J | | 2 days | 3 days |

¹Active Agent

While in accordance with the patent statutes, the best mode and preferred embodiments have been described in detail, the invention is to be measured by the appended claims.

What is claimed is:

1. A floating pesticide dispenser, comprising:
    a floating thermosplastic dispenser containing a pesticide and having a density less than 1.0 grams per cc,
    said thermoplastic dispenser containing a thermoplastic copolymer selected from the group consisting of a copolymer of ethylene-vinyl acetate, a copolymer of ethylene-propylene, and combinations thereof, said ethylene-vinyl acetate copolymer having from about 60 to about 95 percent by weight of ethylene and a weight average molecular weight of from about 40,000 to about 400,000,
    said ethylene-propylene copolymer having from about 30 percent to about 80 percent by weight of ethylene, and a weight average molecular weight of about 50,000 to about 250,000,
    said dispenser containing a pesticide for use in an aqueous environment for destroying aquatic pests,
    said pesticide may be a compound having the formula R$_3$S$_n$X where R$_3$ is selected from the group consisting of an alkyl group having from 1 to 8 carbon atoms, an aryl group, and a substituted aryl group wherein said substituted group is an alkyl or an ester containing from 1 to 6 carbon atoms; X is selected from the group consisting of a halogen, an oxide, an alkoxy OR$^1$ where R$^1$ is an alkyl having from 1 to 12-carbon atoms, or an

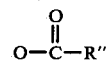

group where R″ is an alkyl having from 1 to 12 carbon atoms, the amount of said pesticide ranging from about 2 parts to about 80 parts by weight per 100 parts of said thermoplastic copolymer when the pesticide is not of formula R$_3$S$_n$X and when said pesticide is said R$_3$S$_n$X compound, the amount of said R$_3$S$_n$X pesticide ranging from about 25 parts to about 75 parts per 100 parts of said copolymer, and
    a weighted anchor, said weighted anchor connected to said dispenser and said pesticide being slowly released from said thermoplastic dispenser.

2. A floating pesticide dispenser according to claim 1, wherein said pesticide is selected from the group consisting of tetramethyl-O,O'-thiodi-p-phenylene phosphorothioate; 2-(1-methylethoxy) phenol methylcarbamate; O,O-diethyl-O-(3,5,6-trichloro-2-pyridyl) phosphorothioate; or O,O-dimethyl phosphorodithioate ester of diethyl mercaptosuccinate, and said R$_3$S$_n$X compound.

3. A floating pesticide dispenser according to claim 2 further including in said dispenser a low density polyethylene thermoplastic, said polyethylene having a molecular weight of from about 100,000 to about 400,000 and existing in an amount of from about 30 percent to about 75 percent based upon the total weight of said polyethylene and said ethylene-vinyl acetate copolymer or said ethylene-propylene copolymer.

4. A floating pesticide dispenser according to claim 1, 2, or 3, including a porosity inducing agent, the amount of said porosity inducing agent ranging from about 5 to about 70 parts by weight per 100 parts of said copolymer when said pesticide is other than said R$_3$S$_n$X compound, the amount of said porosity inducing agent ranging from about 15 to about 70 parts by weight per 100 parts of copolymer when said pesticide is said R$_3$S$_n$X compound, said porosity inducing agent being selected from the group consisting of an oxide and a salt, said oxide and salt having a cation selected from the class consisting of the alkaline metals, the alkaline earth metals, ammonium, iron, zinc, nickel, silver, and tin, and said salt having an anion selected from the class consisting of a carbonate, bicarbonate, nitrate, nitrite, nitride, peroxide, phosphate, phosphite, phosphide, sulfate, sulfite, and sulfide.

5. A floating pesticide dispenser according to claim 4 wherein said pesticide is selected from the group consisting of tetramethyl-O,O'-thiodo-p-phenylene phosphorothioate, tributyltin oxide, and tributyltin fluoride.

6. A floating pesticide dispenser according to claim 5, including from about 0.2 to about 25 parts by weight of a high solubility porosity inducing agent, said high solubility porosity inducing agent selected from the group consisting of the halogenated alkaline metals, the halogenated alkaline earth metals, halogenated iron, halogenated nickel, halogenated zinc, halogenated tin, halogenated silver, ammonium bromide, ammonium carbonate, ammonium chlorate, ammonium chloride, ammonium fluoride, ammonium sulfate, and the like.

7. A floating pesticide dispenser according to claim 5 wherein said porosity inducing agent is selected from the group consisting of magnesium carbonate, magnesium sulfide, magnesium phosphides, magnesium oxide, calcium carbonate, calcium bicarbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, iron carbonate, iron sulfate, iron sulfide, iron sulfite, nickel carbonate, nickel sulfide, zinc carbonate, zinc oxide, zinc sulfide, zinc sulfite, tin oxide, tin sulfide, silver carbonate, silver oxide, silver sulfide, silver sulfite, lithium phosphate, beryllium oxide, strontium carbonate, strontium sulfate, and strontium sulfite.

8. A floating pesticide dispenser according to claim 7 wherein the melt flow index of said ethylene-vinyl acetate copolymer ranges from about 6 to about 12 and the melt flow index of said ethylene-propylene copolymer ranges from about 15 to about 45.

9. A floating pesticide dispenser according to claim 8, wherein said ethylene-vinyl acetate copolymer contains from about 80 to about 93 percent ethylene and has a molecular weight of from about 75,000 to about 300,000, and wherein said ethylene-propylene copolymer contains from about 45 percent to about 75 percent by weight of ethylene and has a molecular weight of from about 100,000 to about 200,000.

10. A floating pesticide dispenser according to claim 9, wherein the amount of said tetramethyl-O,O'-thiodi-p-phenylene phosphorothioate pesticide ranges from about 5 to about 20 parts per 100 parts of said copolymer, and wherein the amount of said tributyltin oxide and said tributyltinfluoride ranges from about 40 parts to about 70 parts per 100 parts of said copolymer.

11. A floating pesticide dispenser according to claim 10, wherein the weight of said anchor is from about 2 to about 10 times the total weight of said floating dispenser.

12. A floating pesticide dispenser according to claim 11, wherein a line connects said anchor and said floating dispenser.

13. A floating pesticide dispenser according to claim 10, wherein said porosity inducing agent is selected from the group consisting of magnesium carbonate, calcium carbonate, ammonium sulfate, barium carbonate, iron carbonate, nickel carbonate, zinc carbonate, and strontium carbonate, and wherein the amount of said porosity inducing agent ranges from about 15 parts to about 35 parts by weight per 100 parts of copolymer when said pesticide is tetramethyl-O,O'-thiodi-p-phenylene phosphorothioate and wherein the amount of said porosity inducing agent is from about 25 parts to about 60 parts by weight when said pesticide is said tributyltin oxide or said tributyltin fluoride.

14. A floating pesticide dispenser according to claim 13 wherein said floating dispenser has a plurality of strands.

15. A floating pesticide dispenser according to claim 13, wherein said porosity inducing agent is calcium carbonate.

16. A floating pesticide dispenser according to claim 15, wherein said floating dispenser has a plurality of strands.

17. A floating pesticide dispenser according to claim 4 wherein said anchor weighs from about 2 to about 10 times the total weight of said floating dispenser.

18. A floating pesticide dispenser according to claim 17, wherein a line connects said anchor and said floating dispenser.

19. A floating pesticide dispenser according to claim 4 wherein said floating dispenser has a plurality of strands.

20. A floating pesticide dispenser according to claim 4, wherein said porosity inducing agent is selected from the group consisting of magnesium carbonate, magnesium sulfide, magnesium phosphides, magnesium oxide, calcium carbonate, calcium bicarbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, iron carbonate, iron sulfate, iron sulfide, iron sulfate, nickel carbonate, nickel sulfide, zinc carbonate, zinc oxide, zinc sulfide, zinc sulfite, tin oxide, tin sulfide, silver carbonate, silver oxide, silver sulfide, silver sulfite, lithium phosphate, beryllium oxide, strontium carbonate, strontium sulfate, and strontium sulfite.

21. A floating pesticide dispenser according to claim 20, wherein said ethylene-vinyl acetate copolymer contains from about 80 to about 93 percent ethylene and has a molecular weight of from about 75,000 to about 300,000, and wherein said ethylene-propylene copolymer contains from about 45 percent to about 75 percent by weight of ethylene and has a molecular weight of from about 100,000 to about 200,000.

22. A floating pesticide dispenser according to claim 21, wherein said porosity inducing agent is selected from the group consisting of magnesium carbonate, calcium carbonate, ammonium sulfate, barium carbonate, iron carbonate, nickel carbonate, zinc carbonate, and strontium carbonate, and wherein the amount of said porosity inducing agent ranges from about 15 parts to about 35 parts by weight per 100 parts of said copolymer except for said $R_3S_nX$ pesticide, the amount of said $R_3S_nX$ pesticide ranging from about 25 parts to about 60 parts by weight per 100 parts of said copolymer.

23. A floating pesticide dispenser according to claim 1, 2, or 3 including from 1 to 60 parts of a high solubility porosity inducing agent, said porosity inducing agent selected from the group consisting of the halogenated alkaline metals, the halogenated alkaline earth metals, the halogenated iron, halogenated nickel, halogenated zinc, halogenated tin, halogenated silver, ammonium bromide, ammonium carbonate, ammonium chlorate, ammonium chloride, ammonium fluoride, ammonium sulfate, and the like.

24. A floating pesticide dispenser according to claim 1, 2, or 3, including a porosity inducing agent, the amount of said porosity inducing agent ranging from about 5 to about 70 parts by weight per 100 parts of said copolymer when said pesticide is other than said $R_3S_nX$ compound, the amount of said porosity inducing agent ranging from about 15 to about 70 parts by weight per 100 parts of copolymer when said pesticide is said $R_3S_nX$ compound, the solubility of said porosity inducing agent being 0.1 grams or less per 100 grams of water.

25. A floating pesticide dispenser according to claim 24, wherein said pesticide is selected from the group consisting of tetramethyl-O,O'-thiodi-p-phenylene phosphorothioate, tributyltin fluoride, and tributyltin oxide.

26. A floating pesticide dispenser according to claim 25, wherein the melt flow index of said ethylene-vinyl acetate copolymer ranges from about 6 to about 12 and the melt flow index of said ethylene-propylene copolymer ranges from about 15 to about 45, wherein said ethylene-vinyl acetate copolymer has a molecular weight of from about 75,000 to about 300,000, and wherein said ethylene-propylene copolymer has a molecular weight of from about 100,000 to about 200,000.

27. A floating pesticide dispenser according to claim 26, wherein said anchor weighs from about 2 to about 10 times the total weight of said floating dispenser.

28. A floating pesticide dispenser according to claim 27, wherein said floating dispenser has a plurality of strands.

29. A floating pesticide dispenser according to claims 1, 2, or 3, including a high solubility porosity inducing agent, the amount of said porosity inducing agent ranging from about 5 to about 70 parts by weight per 100 parts of said copolymer when said pesticide is other than said $R_3S_nX$ compound, the amount of porosity inducing agent ranging from about 15 to about 70 parts by weight per 100 parts of copolymer when said pesticide is said $R_3S_nX$ compound, said porosity inducing agent having a solubility of about 0.1 grams to about 100 grams per 100 grams of water.

30. A floating pesticide dispenser according to claim 29, wherein said pesticide is selected from the group consisting of tetramethyl-O,O'-thiodi-p-phenylene phosphorothioate, tributyltin fluoride, and tributyltin oxide.

31. A floating pesticide dispenser according to claim 30, wherein the melt flow index of said ethylene-vinyl acetate copolymer ranges from about 6 to about 12 and the melt flow index of said ethylene-propylene copolymer ranges from about 15 to about 45, wherein said ethylene-vinyl acetate copolymer has a molecular weight of from about 75,000 to about 300,000, and wherein said ethylene-propylene copolymer has a molecular weight of from about 100,000 to about 200,000.

32. A floating pesticide dispenser according to claim 31, wherein said anchor weighs from about 2 to about 10 times the total weight of said floating dispenser.

33. A floating pesticide dispenser according to claim 32, wherein said floating dispenser has a plurality of strands.

34. A process for destroying aquatic pests by the gradual and continued release of a pesticide for use in an aquatic environment from a floating thermoplastic dispenser, comprising applying said dispenser of said claim 1 to an aquatic environment.

35. A process according to claim 34, wherein said pesticide is selected from the group consisting of tetramethyl-O,O'-thiodi-p-phenylene phosphorothioate, 2-(1-methylethoxy) phenol methylcarbamate; O,O-diethyl-O-(3,5,6-trichloro-2-pyridyl) phosphorothioate; or O,O-dimethyl phosphorodithioate ester of diethyl mercaptosuccinate, and a compound having the formula $R_3S_nX$ where $R_3$ is selected from the group consisting of an alkyl group having from 1 to 8 carbon atoms, an aryl group, and a substituted aryl group wherein said substituted group is an alkyl or an ester containing from 1 to 6 carbon atoms; X is selected from the group consisting of a halogen, an oxide, an alkoxy $OR^1$ where $R^1$ is an alkyl having from 1 to 12 carbon atoms, or an

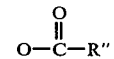

group where R" is an alkyl having from 1 to 12 carbon atoms, the amount of said pesticide other than said $R_3S_nX$ pesticide ranging from about 2 to about 80 parts per 100 parts of said copolymer, the amount of said $R_3S_nX$ pesticides ranging from about 25 parts to about 75 parts per 100 parts of said copolymer.

36. A process according to claim 35, including the further step of adding a low density polyethylene thermoplastic to said dispenser, said polyethylene having a molecular weight of from about 100,000 to about 400,000 and existing in an amount of from about 35 to about 75 percent based upon the total weight of said polyethylene and said ethylene-vinyl acetate copolymer or said ethylene-propylene copolymer.

37. A process according to claim 34, 35, or 36, including the further step of adding a porosity inducing agent to said floating dispenser, the amount of said porosity inducing agent ranging from about 5 to about 70 parts by weight per 100 parts of said copolymer when said pesticide is other than said $R_3S_nX$ compound, the amount of porosity inducing agent ranging from about 15 to about 75 parts by weight per 100 parts of copolymer when said pesticide is said $R_3S_nX$ compound, said porosity inducing agent selected from the group consisting of an oxide and a salt, said oxide and salt having a cation selected from the group consisting of the alkaline metals, the alkaline earth metals, ammonium, iron, zinc, nickel, silver, and tin, and said salt having an anion selected from the group consisting of a carbonate, bicarbonate, nitrate, nitrite, nitride, peroxide, phosphate, phosphite, phosphide, sulfate, sulfite, and sulfide.

38. A process according to claim 37, wherein said pesticide is selected from the group consisting of tetramethyl-O,O'-thiodi-p-phenylene phosphorothioate, tributyltin oxide, and tributyltin fluoride.

39. A process according to claim 38, including from about 0.2 to about 25 parts by weight of a high solubility porosity inducing agent, said high solubility porosity inducing agent selected from the group consisting of the halogenated alkaline metals, the halogenated alkaline earth metals, halogenated iron, halogenated nickel, halogenated zinc, halogenated tin, halogenated silver, ammonium bromide, ammonium carbonate, ammonium chlorate, ammonium chloride, ammonium fluoride, ammonium sulfate, and the like.

40. A process according to claim 38, wherein said porosity inducing agent is selected from the group consisting of ammonium sulfide, ammonium carbonate, magnesium carbonate, magnesium sulfide, magnesium phosphide, magnesium oxide, sodium nitride, calcium carbonate, calcium bicarbonate, calcium nitride, calcium oxide, calcium phosphate, calcium phosphite, calcium sulfide, calcium sulfite, barium carbonate, barium nitride, barium peroxide, barium phosphite, barium sulfate, barium sulfite, iron carbonate, iron sulfate, iron sulfide, iron sulfite, nickel carbonate, nickel sulfide, zinc carbonate, zinc oxide, zinc sulfide, zinc sulfite, tin sulfide, tin oxide, silver carbonate, silver oxide, silver sulfide, silver sulfite, lithium phosphate, beryllium oxide, strontium carbonate, strontium sulfate, and strontium sulfite.

41. A process according to claim 40, wherein the melt flow index of said ethylene-vinyl acetate copolymer ranges from about 6 to about 12 and the melt flow index of said ethylene-propylene copolymer ranges from about 15 to about 45.

42. A process according to claim 41, wherein said ethylene-vinyl acetate copolymer contains from about 80 to about 93 percent ethylene and has a molecular weight of from about 75,000 to about 300,000 and wherein said ethylene-propylene copolymer contains from about 45 percent to about 75 percent by weight of ethylene and has a molecular weight of from about 100,000 to about 200,000.

43. A process according to claim 42, wherein the amount of said anchor is from about 2 to about 10 times the total weight of said floating dispenser.

44. A process according to claim 43, wherein the line connects said anchor and said floating dispenser.

45. A process according to claim 44, wherein the line connects said anchor and said floating dispenser.

46. A process according to claim 42, wherein the amount of said tetramethyl-O,O'-thiodi-p-phenylene phosphorothioate pesticide ranges from about 5 to about 20 parts per 100 parts of said copolymer, and wherein the amount of said tributyltin oxide and said tributyltinfluoride ranges from about 40 parts to about 70 parts per 100 parts of said copolymer.

47. A process according to claim 46, wherein said porosity inducing agent is selected from the group consisting of magnesium carbonate, calcium carbonate, ammonium sulfate, ammonium carbonate, iron carbonate, nickel carbonate, zinc carbonate, silver carbonate and strontium carbonate, and wherein the amount of said porosity inducing agent ranges from about 15 parts to about 35 parts by weight per 100 parts of copolymer when said pesticide is tetramethyl-O,O'-thiodi-p-phenylene phosphorothioate and wherein the amount of said porosity inducing agent is from about 25 parts to about 60 parts by weight when said pesticide is said tributyltin oxide or said tributyltin fluoride.

48. A process according to claim 47, wherein said porosity inducing agent is calcium carbonate.

49. A process according to claim 48, wherein said floating dispenser is a plurality of strands.

50. A process according to claim 37, wherein said porosity inducing agent is selected from the group consisting of magnesium carbonate, magnesium sulfide, magnesium phosphides, magnesium oxide, calcium carbonate, calcium bicarbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, iron carbonate, iron sulfate, iron sulfide, iron sulfite, nickel carbonate, nickel sulfide, zinc carbonate, zinc oxide, zinc sulfide, zinc sulfite, tin oxide, tin sulfide, silver carbonate, silver oxide, silver sulfide, silver sulfite, lithium phosphate, beryllium oxide, strontium carbonate, strontium sulfate, and strontium sulfite.

51. A process according to claim 50, wherein said ethylene-vinyl acetate copolymer contains from about 80 to about 93 percent ethylene and has a molecular weight of from about 75,000 to about 300,000, and wherein said ethylene-propylene copolymer contains from about 45 percent to about 75 percent by weight of ethylene and has a molecular weight of from about 100,000 to about 200,000.

52. A process according to claim 51, wherein said porosity inducing agent is selected from the group consisting of magnesium carbonate, calcium carbonate, ammonium sulfate, barium carbonate, iron carbonate, nickel carbonate, zinc carbonate, and strontium carbonate, and wherein the amount of said porosity inducing agent ranges from about 15 parts to about 35 parts by weight per 100 parts of said copolymer except for said $R_3S_nX$ pesticide, the amount of said $R_3S_nX$ pesticide ranging from about 25 parts to about 60 parts by weight per 100 parts of said copolymer.

53. A process according to claim 37, wherein said floating dispenser is a plurality of strands.

54. A process according to claim 37, wherein said anchor weighs from about 2 to about 10 times the total weight of said floating dispenser.

55. A process according to claim 34, 35, or 36, including from 1 to 60 parts of a high solubility porosity inducing agent, said porosity inducing agent selected from the group consisting of the halogenated alkaline metals, the halogenated alkaline earth metals, halogenated iron, halogenated nickel, halogenated zinc, halogenated tin, halogenated silver, ammonium bromide, ammonium carbonate, ammonium chlorate, ammonium chloride, ammonium fluoride, ammonium sulfate, and the like.

56. A process according to claims 34, 35, and 36 wherein said porosity inducing agent ranges from about 5 to about 70 parts by weight per 100 parts of said copolymer when said pesticide is other than said $R_3S_nX$ compound, the amount of said porosity inducing agent ranging from about 15 to about 70 parts by weight per 100 parts of copolymer when said porosity inducing agent is said $R_3S_nX$ compound, the solubility of said porosity inducing agent being 0.1 grams or less per 100 grams of water.

57. A process according to claim 56, wherein said pesticide is selected from the group consisting of tetramethyl-O,O'-thiodi-p-phenylene phosphorothioate, tributyltin fluoride, and tributyltin oxide.

58. A process according to claim 57, wherein the melt flow index of said ethylene-vinyl acetate copolymer ranges from about 6 to about 12 and the melt flow index of said ethylene-propylene copolymer ranges from about 15 to about 45, wherein said ethylene-vinyl acetate copolymer has a molecular weight of from about 75,000 to about 300,000, and wherein said ethylene-propylene copolymer has a molecular weight of from about 100,000 to about 200,000.

59. A process according to claim 58, wherein said anchor weighs from about 2 to about 10 times the total weight of said floating dispenser.

60. A process according to claim 59, wherein said floating dispenser has a plurality of strands.

61. A process according to claims 34, 35 and 36, including a high solubility porosity inducing agent, the amount of said porosity inducing agent ranges from about 5 to about 70 parts by weight per 100 parts of said copolymer when said pesticide is other than said $R_3S_nX$ compound, the amount of porosity inducing agent ranges from about 15 to about 70 parts by weight per 100 parts of copolymer when said pesticide is said $R_3S_nX$ compound, said porosity inducing agent having a solubility of from about 0.1 grams to about 100 grams per 100 grams of water.

62. A process according to claim 61, wherein said pesticide is selected from the group consisting of tetramethyl-O,O'-thiodi-p-phenylene phosphorothioate, tributyltin fluoride, and tributyltin oxide.

63. A process according to claim 62, wherein the melt flow index of said ethylene-vinyl acetate coppolymer ranges from about 6 to about 12 and the melt flow index of said ethylene-propylene copolymer ranges from about 15 to about 45, wherein said ethylene-vinyl acetate copolymer has a molecular weight of from about 75,000 to about 300,000, and wherein said ethylene-propylene copolymer has a molecular weight of from about 100,000 to about 200,000.

64. A process according to claim 63, wherein said anchor weighs from about 2 to about 10 times the toal weight of said floating dispenser.

65. A process according to claim 64, wherein said floating dispenser has a plurality of strands.

* * * * *